United States Patent [19]

Hart

[11] Patent Number: 5,626,614

[45] Date of Patent: May 6, 1997

[54] T-ANCHOR SUTURING DEVICE AND METHOD FOR USING SAME

[75] Inventor: Charles C. Hart, Huntington Beach, Calif.

[73] Assignee: Applied Medical Resources Corporation, Laguna Hills, Calif.

[21] Appl. No.: 577,651

[22] Filed: Dec. 22, 1995

[51] Int. Cl.$^6$ .................................................. A61B 17/04
[52] U.S. Cl. ........................... 606/232; 606/144; 606/147
[58] Field of Search ........................... 606/232, 144, 606/145, 147, 148, 139, 108; 604/51

[56] References Cited

U.S. PATENT DOCUMENTS

| | | |
|---|---|---|
| Re. 34,021 | 8/1992 | Mueller et al. . |
| 4,669,473 | 6/1987 | Richards et al. ........................ 606/232 |
| 5,071,405 | 12/1991 | Piontek et al. . |
| 5,207,679 | 5/1993 | Li ........................................... 606/232 |
| 5,429,598 | 7/1995 | Waxman et al. . |
| 5,470,337 | 11/1995 | Moss ....................................... 606/232 |

Primary Examiner—Michael Powell Buiz
Assistant Examiner—Kevin Truong
Attorney, Agent, or Firm—Richard L. Myers

[57] ABSTRACT

A surgical apparatus includes a needle having an outer surface and an anchor bar disposed in sliding engagement with the needle. A suture has a first end attached to the anchor bar and a second end extending laterally of the anchor bar and outwardly of the needle. A pusher is movable coaxially of the needle to engage the anchor bar and to separate the anchor bar from the needle to form an anchor relative to a body wall. The anchor bar may have an outer surface with an inclined relationship to its longitudinal axis in order to facilitate axial insertion of the anchor bar through the body wall. An associated method for anchoring a pair of body walls includes the step of attaching a bolster to the second end of the suture and separating the anchor bar from the needle with the anchor bar and the first end of the suture disposed on one side of the body wall and the second end of the suture disposed on the other side of the body wall.

21 Claims, 4 Drawing Sheets

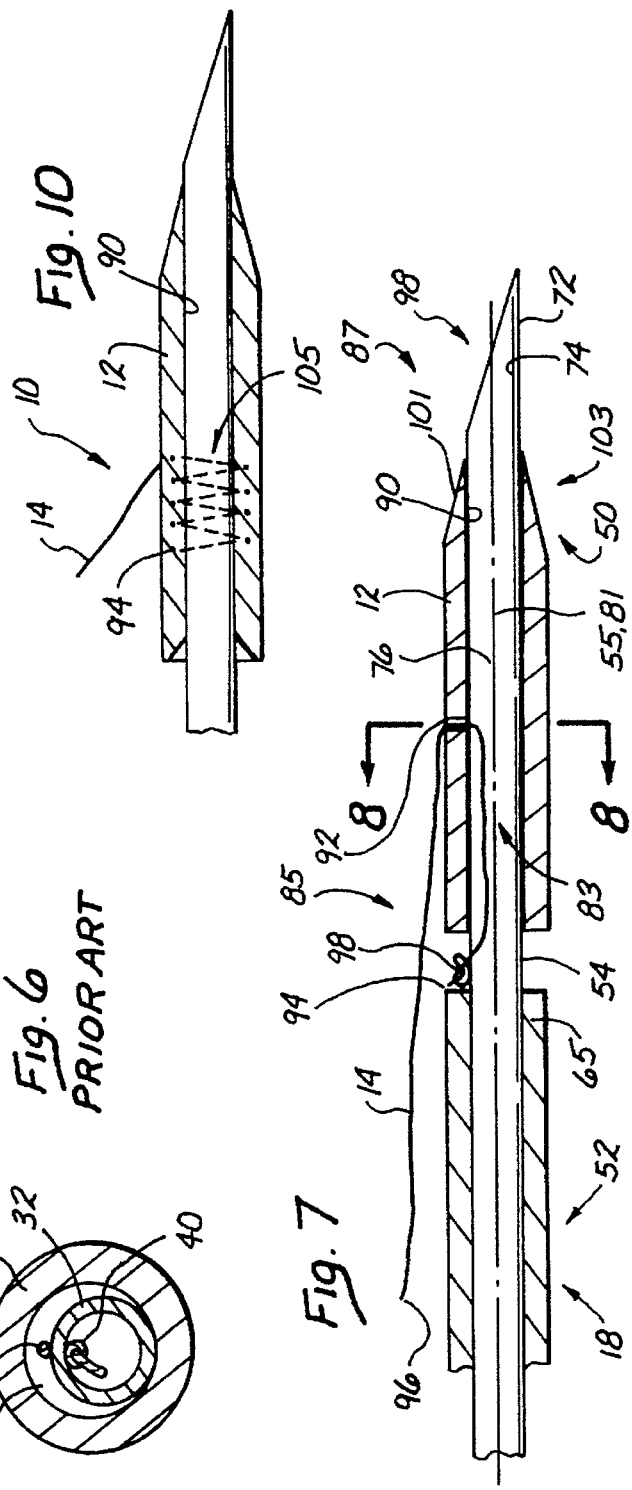

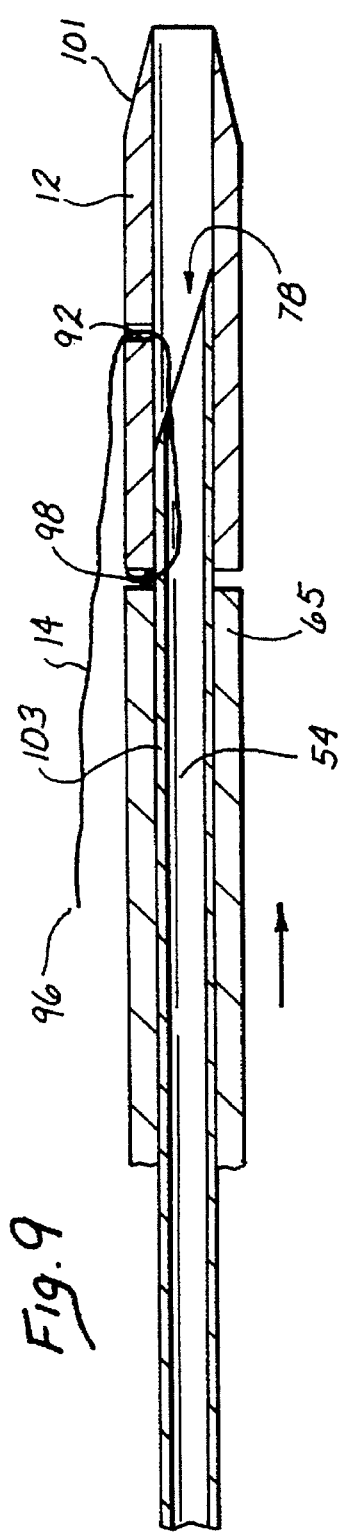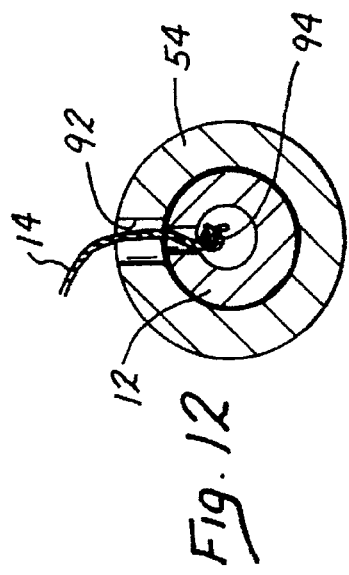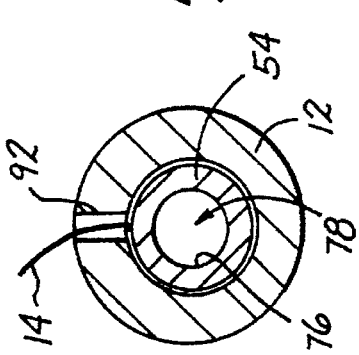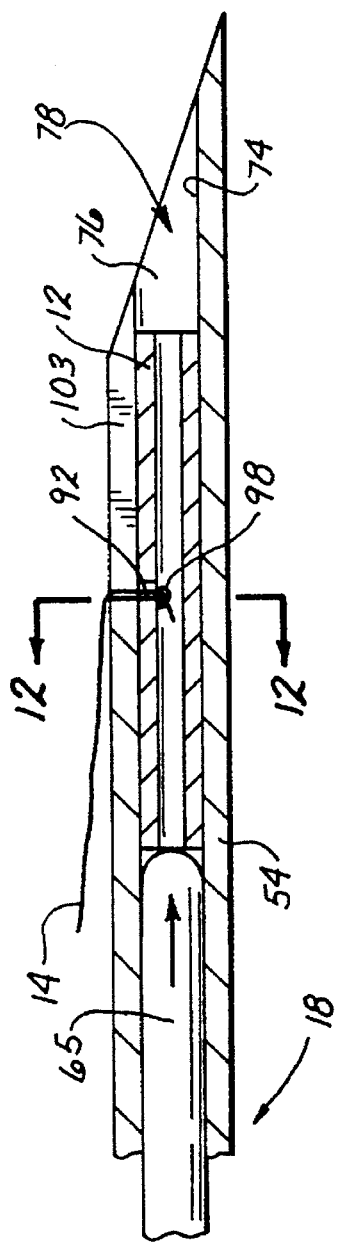

T-ANCHOR SUTURING DEVICE AND METHOD FOR USING SAME

BACKGROUND OF THE INVENTION

1. Field of the Invention

This invention relates generally to surgical attachment devices and more specifically to T-anchors adapted for maintaining body walls in proximity.

2. Discussion of the Prior Art

A T-anchor is a surgical device used for moving two body walls into proximity and for maintaining those two walls in proximity for an extended period of time. Such an apparatus could be valuable for many surgical procedures such as the installation of a feeding tube into the stomach of a patient as disclosed and claimed by applicant in U.S. Pat. No. 5,429,598 issued on Jul. 4, 1995, and entitled Surgical Access Device and Procedure. In this procedure, a T-anchor could be used to move the wall of the stomach into proximity with the abdominal wall prior to installation of a feeding tube.

The T-anchor typically consists of an anchor bar having a longitudinal configuration and a suture attached to the bar and extending laterally from the bar. An introducer can be used to pass the anchor bar through the two walls and to deploy the anchor bar on the far side of the second wall. The suture is left to extend through the two walls, and is provided with a bolster on the near side of the two walls which is slidable along the suture. As the suture is pulled and the bolster is pushed, the anchor bar seats against the second wall which is drawn into proximity with the first wall. A knot tied in the suture on the proximal side of the bolster maintains the anchor in this operative position with the two walls in close proximity.

In the past, the T-anchor has been loaded into the proximal end of a hollow needle which has been inserted through the two walls. The anchor bar was then expelled using a guidewire, from the lumen of the needle on the far side of the second wall. In this system the suture attached to the anchor bar, extends proximally through the entire lumen of the needle. After the anchor bar has been deployed, the needle is withdrawn backwardly through the two walls and along the suture. The bolster is then threaded onto the suture and the procedure completed as previously noted.

In this embodiment of the T-anchor assembly, the lumen of the needle or introducer must be sufficiently large to accommodate not only the diameter of the anchor bar, but also the diameter of the suture. Both of these elements must occupy space side-by-side within the lumen. This requirement for an increased inside diameter of the lumen has of course demanded a larger outside diameter for the needle.

It is always of interest to simplify apparatus and procedures for medical application since this ultimately results in reduced time, trauma and cost. It is also of interest to reduce the size of incisions or punctures required by various procedures in order to promote healing and reduce trauma for the patient.

SUMMARY OF THE INVENTION

These and other deficiencies of the T-anchors and introducers of the prior art are overcome with the present invention which provides for introduction of the anchor bar with the suture positioned exteriorly of the needle. This provides several advantages. First, the procedure can be shortened by at least one step since the bolster can be preattached to the suture by the manufacturer. Another advantage is achieved with the reduced size requirements for the needle or introducer. Since the suture is not positioned within the lumen of the needle, the diameter of the needle can be reduced accordingly.

In one embodiment, the anchor bar is positioned outwardly of the needle. Such an embodiment can be achieved using either a solid or hollow needle having a significantly reduced outside diameter. In this case, the maximum diameter is dictated by the diameter of the anchor bar, not the needle. This embodiment is further characterized by the formation of a conical taper at the distal end of the anchor bar. While this taper facilitates introduction of the assembly through the walls, it nevertheless retains a blunt distal end when the anchor bar is deployed from the needle. In a specific embodiment, the T-anchor is formed with the suture embedded in the wall of the anchor bar. This even further reduces the diametral requirements of the assembly.

In a further embodiment of the invention, the needle of the introducer is provided with an axial hole at its distal end and an radial slot extending proximally from the hole. This slotted introducer is of advantage in an embodiment wherein the T-anchor is disposed interiorly of the needle lumen. In this case the suture, which must extend from the lumen outwardly of the needle, can be threaded through the radial slot and the axial opening. A pusher can then be used to deploy the anchor bar from the lumen of the needle as the needle is withdrawn with the suture passing along the slot and through the opening to clear the needle.

In one aspect of the invention, a surgical anchor device is adapted for insertion through a body wall. The anchor device includes an anchor bar extending longitudinally along an axis between a proximal end and a distal end. A suture having a first end and a second end is disposed with its first end in a fixed relationship with the anchor bar between the distal end and the proximal end of the anchor bar. Portions of the anchor bar disposed at the distal end define an outer surface having an inclined relationship with the axis of the anchor bar. The inclined outer surface at the distal end of the anchor bar facilitates axial insertion of the anchor device through the body wall. In a preferred embodiment, the inclined outer surface has the configuration of a cone.

In another aspect of the invention, a surgical apparatus is adapted to be inserted through a body wall and to form an anchor relative to the body wall. The apparatus includes a needle having an outer surface, and an anchor bar having a longitudinal configuration and being adapted for slidable disposition relative to the needle. A suture is disposed with its first end attached to the anchor bar and a second end extending laterally of the anchor bar and outwardly of the outer surface of the needle. A pusher is movable coaxially of the needle to engage the anchor bar and to separate the anchor bar from the needle to form the anchor relative to the body wall. This anchor bar can be disposed either inside the needle or outside the needle. In the former case, the needle includes radial portions defining an axial opening at the distal end of the needle and longitudinal portions defining a radial slot extending from the axial opening proximally of the needle.

In a method associated with the present invention, a needle, anchor bar and suture are provided for engaging and holding a pair of body walls in close proximity. The first end of the suture is attached to the anchor bar and the anchor bar mounted relative to the needle with the suture extending outwardly of the outer surface of the needle. A bolster is attached to the second end of the suture. Then the needle and anchor bar are inserted through the body walls, and the anchor bar separated from the needle with the anchor bar and the first end of the suture disposed on one side of the body walls and the bolster and second end of the suture disposed on the other side of the body walls. The needle is removed and the bolster fixed along the suture to anchor the pair of body walls in close proximity to each other.

These and other features and advantages of the invention will become more apparent with the description of preferred embodiments and reference to the associated drawings.

DESCRIPTION OF THE DRAWINGS

FIG. 1 is a perspective view of a T-anchor and introducer extending through body walls including an abdominal wall and a stomach wall;

FIG. 2 is a perspective view similar to FIG. 1 illustrating an anchor bar and suture of the T-anchor, being deployed from the introducer;

FIG. 3 is a perspective view similar to FIG. 1 with the introducer removed and the suture pulled to draw the two body walls into proximity;

FIG. 4 is a perspective view similar to FIG. 1 illustrating the bolster operatively positioned against the first body wall and the anchor bar operatively positioned against the second body wall to maintain the two walls in proximity;

FIG. 5 is an axial cross-section view of a needle and T-anchor of the prior art;

FIG. 6 is a cross-section view taken along lines 6—6 of FIG. 5;

FIG. 7 is an axial cross-section view of one embodiment of the T-anchor and introducer of the present invention with the anchor bar positioned outwardly of the needle;

FIG. 8 is a radial cross-section view taken along lines 8—8 of FIG. 7;

FIG. 9 is an axial cross-section view similar to FIG. 7 illustrating a pusher tube being operated to deploy the anchor bar;

FIG. 10 is an axial cross-section view of an anchor bar having a suture molded within the wall of the anchor bar;

FIG. 11 is an axial cross-section view of a further embodiment of the invention wherein the anchor bar is disposed interiorly of the needle and the suture extends through a radial slot in the needle; and FIG. 12 is a radial cross-section view taken along lines 12—12 of FIG. 11.

DESCRIPTION OF PREFERRED EMBODIMENTS AND BEST MODE OF THE INVENTION

Figure 1:
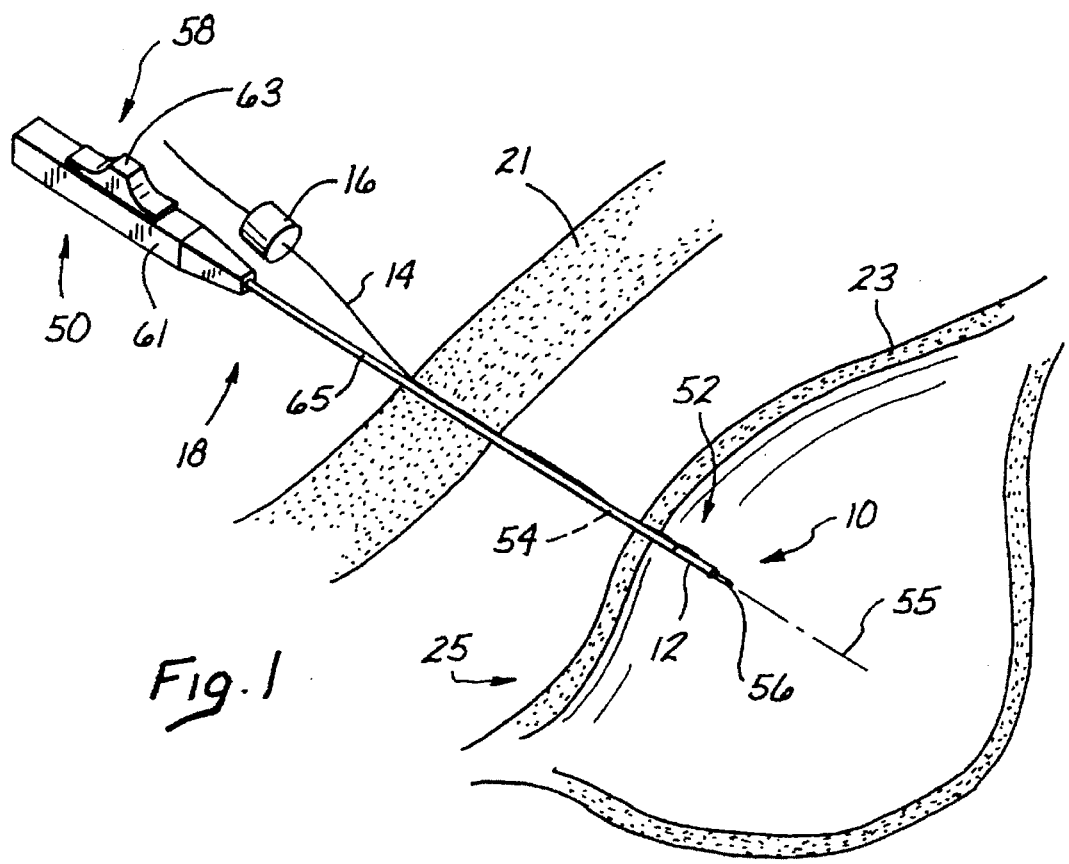
FIG. 1–FIG. 4 illustrate steps in a method associated with the present invention.

A T-anchor is illustrated in FIG. 1 and designated generally by the reference numeral 10. The T-anchor 10 includes an anchor bar 12 and attached suture 14. A bolster 16 is slidable along the suture 14. Also illustrated in FIG. 1 are an introducer 18, an abdominal wall 21, and a stomach wall 23 which forms a stomach 25.

Figure 2:
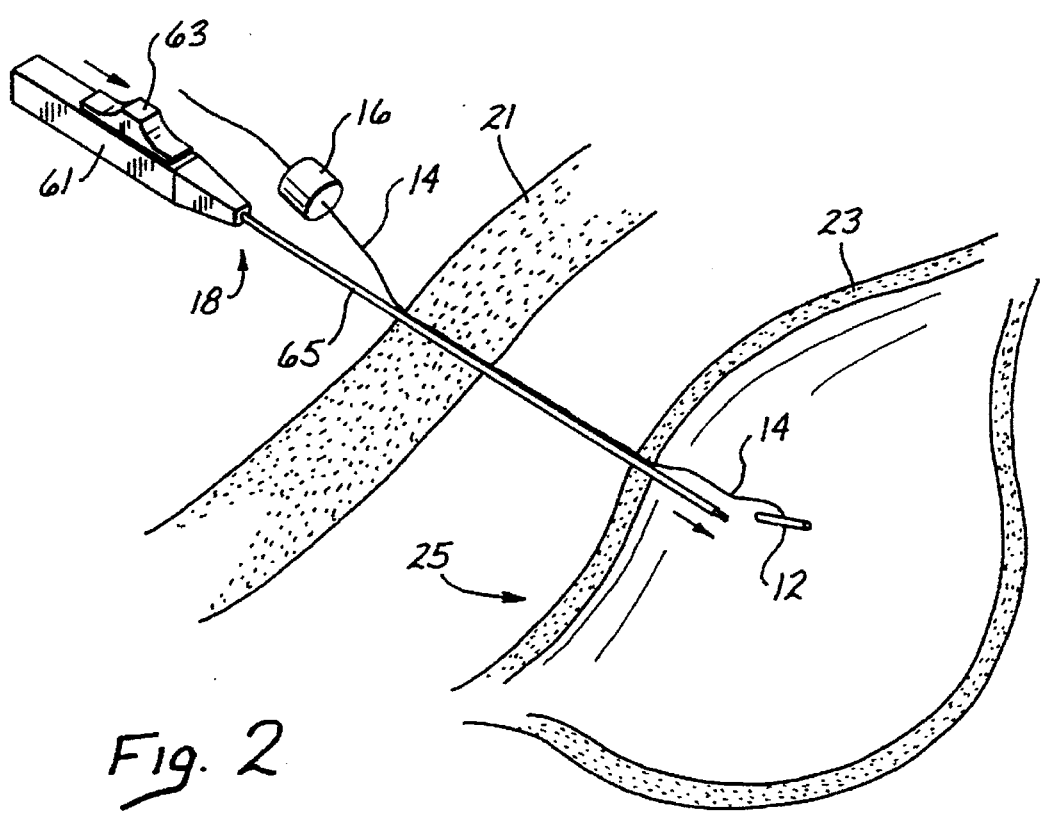
Figure 3:
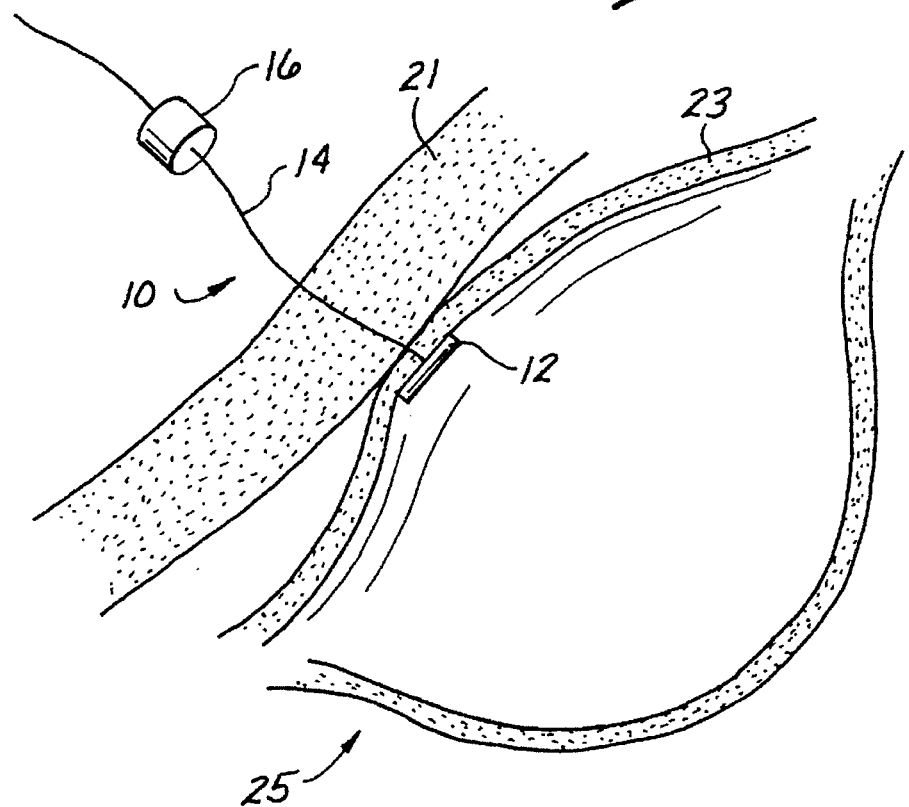
Figure 4:
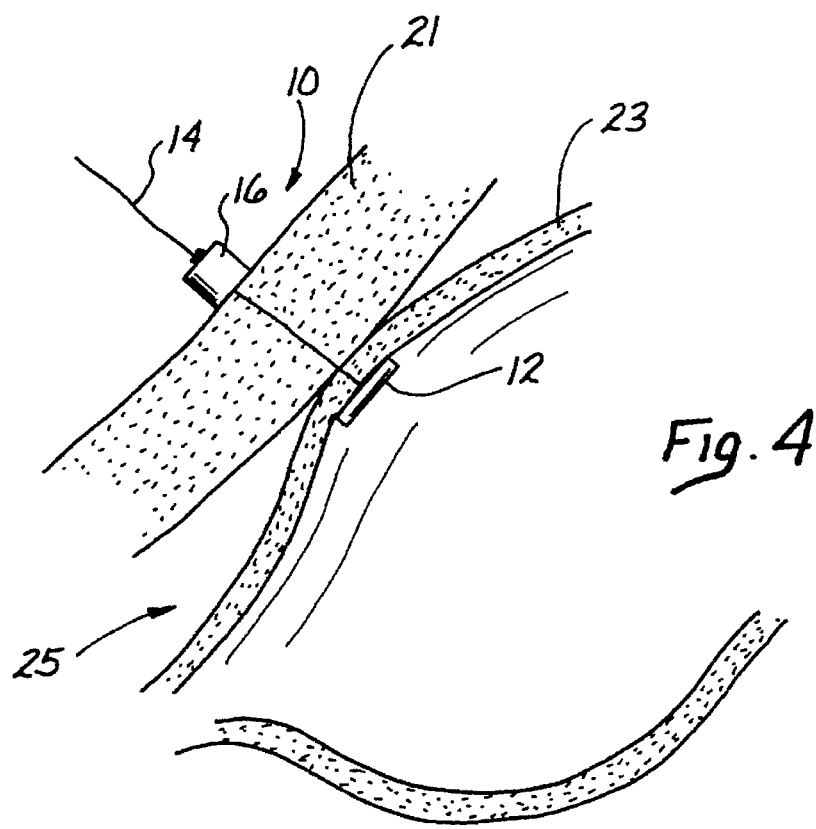

It is the purpose of the introducer 18 to position the suture 14 through the body walls 21, 23 with the anchor bar 12 disposed on the far side of the wall 23 and the bolster 16 disposed on the near side of the wall 21. The T-anchor 10 can then be deployed from the introducer 18 as illustrated in FIG. 2. AFter the T-anchor 10 hs been deployed, the introducer 18 is withdrawn and the suture 14 pulled taut. Tensioning the suture 14 tends to seat the anchor bar 12 against the stomach wall 23 and also to draw the stomach wall 23 into proximity with the abdominal wall 21. This operation of the T-anchor is best illustrated in FIG. 3. Once the two walls 21 and 23 have been brought into proximity, this relationship can be maintained by sliding the bolster 16 along the suture 14 until it abuts the abdominal wall 21. With the T-anchor thus operatively disposed, the suture 14 can be knotted proximally of the bolster 16 to maintain the anchor bar 12 and bolster 16 in a fixed relationship, with the walls 21 and 23 maintained in close proximity.

A T-anchor 30 representative of the prior art is illustrated in FIGS. 5 and 6. This T-anchor 30 of the prior art, which also includes an anchor bar 32 and suture 34, is operatively positioned using a needle 36 having an interior lumen 38 and an axial opening 41 at its distal end. Using this apparatus of the prior art, the T-anchor 30 is adapted for disposition within the lumen 38 of the needle 36. When the anchor bar 32 is operatively positioned within the lumen 38, the suture 34 is threaded proximally through the lumen 38 to exit the needle 36 at its proximal end. With this arrangement, the anchor bar 32 must share the lumen 38 with the suture 34. Accordingly the lumen 38 and the needle 36 must be larger than required by the anchor bar 32. This is particularly apparent in the cross-sectional view of FIG. 6. The suture is threaded through a hole in the anchor bar 32 and provided with a knot 40 to fix the end of the suture 34.

With this apparatus of the prior art, the anchor bar 32 is deployed by a guidewire 43 which is moved distally through the lumen 38 to move the anchor bar 32 through the opening 41. Unfortunately, this step still leaves the suture 34 within the lumen 38. In order to withdraw the needle 36 from the operative site, it must be moved proximally until it clears the free end of the suture 34. Since this free end must pass through the lumen 38, it is impossible to thread the bolster 16 over the suture 34 until the needle 36 has been withdrawn. These structural deficiencies of course adds several steps to this process of the prior art.

Returning now to FIG. 1, a preferred embodiment of the invention is illustrated to include the introducer 18 having a distal end 50 and a proximal end 52. A needle 54, having an axis 55, is disposed at the distal end 50 and provided with a sharped tip 56. A handle assembly 58 is disposed at the proximal end 52 of the introducer 18. The assembly 58 includes a handle 61, and a thumb tab 63 which is slidable longitùdinally relative to the handle 61 to deploy the anchor bar 12 as illustrated in FIG. 2. The introducer 18 also includes a pusher 65 which has a tubular configuration in this embodiment. This push tube 65 is disposed over the needle 54 and is axially movable relative to the needle 54.

In this particular embodiment, the anchor bar 12 is disposed outwardly of the needle 54 as best illustrated in the enlarged view of FIG. 7. From this view it can be seen that the needle 54 may have a tubular configuration with a wall 70 defined by an outer surface 72 and an inner surface 74 which forms a lumen 76. The wall 70 is provided with a sharpened tip 78 at the distal end 50 of the introducer 18.

The anchor bar 12 has a longitudinal tubular configuration in the embodiment of FIG. 7 and is characterized by an axis 81 which is disposed coaxially with the axis 55 of the needle 54. A channel 83 is formed axially of the anchor bar 12 and extends between a proximal end 85 and a distal end 87 of the anchor bar 12. This channel 83 is defined by an inner surface 90 which slidably engages the outer surface 72 of the needle 78 in this embodiment.

A radial bore 92 is provided through the wall of the anchor bar 12. The suture 14, having a first end 94 and a second end 96, is threaded through the bore 92 where the first end 94 is provided with a knot 98. The knot 98 is formed sufficiently large that it will not pass through the radial bore 92. With this particular embodiment, the anchor bar 12 is disposed outwardly of the needle 54 and generally determines the maximum diameter for the introducer 18.

During introduction of the anchor bar 12, the sharpened tip 78 of the needle 54 initially punctures the body walls 22, 23. With the further distal movement of the introducer 18, the wall 21 contacts the distal end 87 of the anchor bar 12. In order to minimize insertion forces, the distal end 87 of the anchor bar 12 can be provided with an inclined surface which dilates the tissue defining the hole through the wall 21. This tissue slides up on the inclined surface 101 until it reaches the outside diameter of the anchor bar 12. In a preferred embodiment, the inclined surface 101 is formed in the shape of a cone with an outer circumference which decreases with progressive distal positions along the axis 81.

The handle assembly 58 can be constructed in the manner disclosed by applicant in U.S. Pat. No. 5,443,449 issued Aug. 22, 1995 and entitled Cholangiography Catheter. In such a device operation of the thumb tab 63 relative to the handle 61 can be relied on to move the push element 65 relative to the needle 54. In one embodiment, the needle 54 is fixed to the handle 61 and operation of the thumb tab 63 moves the push element 65 relative to the stationary handle 61 and needle 54. In another embodiment, the handle 61 and push element 65 are disposed in a fixed relationship. In this case, operation of the thumb tab 63 moves the needle relative to the handle 61 and the push element 65.

With the inner surface 90 of the anchor bar 12 disposed in close proximity to the outer surface 72 of the needle 54, there is no room to accommodate the suture 14 or the knot 98 between these two surfaces. In the embodiment illustrated in FIG. 7, the needle 54 has a hollow configuration making it possible for the lumen 76 to receive the suture 14. Even in this embodiment, however the suture 14 must extend not only through the bore 92 in the anchor bar 12, but also the wall 70 of the needle 54.

Competing with this interest in providing space for the suture 14 is the requirement that the anchor bar 12 be slidable distally on the needle 54 to deploy the T-anchor 10. This requires that the opening 78 be extended longitudinally in order that the suture 14 within the lumen 76 can be passed out of the opening 78. In the illustrated embodiment, the opening 78 includes not only an axial opening which faces distally of the needle 54, but also a lateral opening in the form of a slot 103 Which extends along the wall 70 parallel to the axis 81. With the slot 103 extending distally to the opening 78, the push element 65 can be activated to move the anchor bar 12 distally of the needle 54. As this movement proceeds, the suture 14, interiorly of the inner surface of the anchor bar 12, moves along the slot 101 and the opening 78 to free the T-anchor 10.

When the push element 65 is operated to deploy the anchor bar 12, as illustrated in FIG. 9, the T-anchor 10 is completely freed of the introducer 18. Importantly, with this embodiment the suture 14 is no longer present within the lumen 76 so withdrawal of the introducer 18 is not dictated by the configuration of the suture 14 at the second end 96. This enables the bolster 16 to be preattached to the suture 14 thereby eliminating an attachment step which would otherwise be required during the surgical procedure. The needle 54 can be sufficiently small that the lumen 76 can be sized to accommodate only the narrow suture 14. This will also facilitate a reduction in the outside diameter of the anchor bar 12, resulting in a smaller hole through the walls 21, 23 with commensurate reduction in trauma and healing time for the patient.

A further embodiment of the T-anchor 10, best illustrated in FIG. 10, is of particular interest to this invention. In this case, the anchor bar 12 is injection molded over the first end 94 of the suture 14. In a preferred embodiment, this first end 94 takes the form of a spiral 105 which can be fully and completely fixed within the molded walls of the T-anchor 12. With this construction of the T-anchor 10, there is no requirement for space interiorly of the inner surface 90 in order to accommodate the suture 14 or knot 98. Accordingly, no slot 103 need be provided, and in fact, the needle 54 can have a solid rather than a hollow configuration. Even in this embodiment, it will be noted that the suture 14 is mounted on the introducer 18 with its second end 96 extending outwardly of the outer surface 72 of the needle 54.

This same valuable feature is found in a further embodiment of the invention illustrated in FIG. 11. In this case, the anchor bar 12 is disposed interiorly of the lumen 76 of the needle 54. As opposed to the constructions of the prior art, the outer surface of the anchor bar 12 is in full sliding engagement with the inner surface 74 of the needle 54. No extra space need be provided for the suture 14 which extends outwardly from the tubular anchor bar 12 through the bore 92 and the slot 103. In this embodiment, the push element 65 can be formed as a solid shaft sufficiently small to move axially through the lumen 76. As the anchor bar 12 is expelled from the needle 54, the suture 14 moves along the slot 103 and into the opening 78 as the anchor bar 12 and suture 14 are freed from the introducer 18. In this embodiment, the anchor bar 12 can be tubular to accommodate the knot 98, or alternatively, the anchor bar 12 can have a solid configuration where the first end 94 of the suture 14 is embedded as illustrated in the cross-sectional view of FIG. 12.

From the foregoing discussion of preferred embodiments, it will be noted that many variations on the concept will now be obvious to those skilled in the art. For example, the opening 78 at the distal end 50 of the needle 54 can be shaped in any configuration facilitating the piercing of the walls 21, 23. Similarly, the inclined surface 101 can be formed in other than a conical configuration to reduce friction forces developed during introduction of the T-anchor 10. Although the needle 54 will typically be constructed of stainless steel, both the anchor bar 12 and push element 65 can be formed from any body compatible plastic such as polypropylene. In a particular embodiment, the anchor bar may be formed from a resorbable material such as polyglycolic acid. It will also be appreciated that in a particular embodiment, the anchor bar 12 can be either hollow as illustrated in FIG. 5, or solid as illustrated in FIG. 12. Also, the needle 54 can be hollow as illustrated in FIG. 7 or solid as illustrated in FIG. 10.

Given these wide variations, which are all within the scope of this concept, one is cautioned not to restrict the invention to the embodiments which have been specifically disclosed and illustrated, but rather encouraged to determine the scope of the invention only with reference to the following claims.

I claim:

1. Surgical apparatus adapted to be inserted through a body wall and to form an anchor relative to the body wall, comprising:

a needle having an outer surface;

an anchor bar having a longitudinal configuration and being adapted for disposition relative to the needle in sliding engagement with the outer surface of the needle;

a suture having a first end and a second end, the first end of the suture being attached to the anchor bar with the second end of the suture extending laterally of the anchor bar and outwardly of the outer surface of the needle when the anchor bar is disposed relative to the needle; and a pusher movable coaxially of the needle to engage the anchor bar and to separate the anchor bar from the needle to form the anchor relative to the body wall.

2. The surgical apparatus recited in claim 1 wherein:

the anchor bar has the configuration of a tube with an inner surface defining a longitudinal channel through the anchor bar; and the anchor bar is adapted for disposition outside the needle with the inner surface of the anchor bar in sliding engagement with the outer surface of the needle.

3. The surgical apparatus recited in claim 1 wherein:

the needle has the configuration of a tube with an inner surface defining a longitudinal channel extending through the needle; and the anchor bar is adapted for disposition inside the longitudinal channel of the needle.

4. The surgical apparatus recited in claim 1 wherein:

the anchor bar has an inner surface and with the inner surface of the anchor bar in sliding engagement with the outer surface of the needle; and the pusher comprises a hollow tube disposed over the needle and slideable distally along the outer surface of the needle to engage the anchor bar and to separate the anchor bar from the needle.

5. The surgical apparatus recited in claim 4 wherein the anchor bar has a distal end and a proximal end and the device further comprises:

portions of the anchor bar at the distal end of the anchor bar defining an outer surface with a conical configuration facilitating insertion of the anchor bar through the body wall.

6. A method for anchoring a pair of body walls in close proximity to each other, including the steps of:

providing a needle having an outer surface and an axis extending between a proximal end and a distal end;

providing an anchor bar having an outer surface;

providing a suture having a first end and a second end;

attaching the first end of the suture to the anchor bar;

positioning the anchor bar and the suture relative to the needle with the anchor bar in sliding engagement with the outer surface of the needle and with the second end of the suture extending outwardly of the outer surface of the needle;

attaching a bolster to the second end of the suture;

inserting the needle and the anchor bar through the pair of body walls;

separating the anchor bar from the needle with the anchor bar and the first end of the suture disposed on one side of the pair of body walls and the bolster and second end of the suture disposed on the other side of the pair of body walls;

removing the needle from the body wall; and fixing the bolster along the suture to anchor the pair of body walls in close proximity to each other.

7. The method recited in claim 6 wherein:

the second providing step includes the step of providing the anchor bar with an inner surface defining a longitudinal channel extending through the anchor bar between a distal end and a proximal end of the anchor bar; and the mounting step includes the step of mounting the anchor bar on the needle with the inner surface of the anchor bar in sliding relationship with the outer surface of the needle.

8. The method recited in claim 7 wherein the step of providing the anchor bar includes the step of shaping the anchor bar to form a conical surface at the distal end of the anchor bar.

9. The method recited in claim 6 wherein:

the first providing step includes the step of providing the needle with an inner surface defining a longitudinal channel extending through the needle between a distal end and a proximal end of the needle; and the mounting step includes the step of mounting the anchor bar in the longitudinal channel of the needle with the outer surface of the anchor bar in sliding relationship with the inner surface of the needle.

10. A surgical anchor device adapted for insertion through a body wall, comprising:

an anchor bar extending longitudinally along an axis between a proximal end and a distal end, the anchor bar having a longitudinal side surface and an end surface;

the end surface of the anchor bar having a conical configuration;

a suture having a first end and a second end, the first end of the suture having a fixed relationship with the anchor bar between the distal end and the proximal end of the anchor bar;

portions of the anchor bar disposed at the distal end of the anchor bar and defining an outer surface having an inclined relationship with the axis of the anchor bar; whereby the inclined outer surface at the distal end of the anchor bar facilitates axial insertion of the anchor device through the body wall.

11. The surgical anchor device recited in claim 10 wherein the end surface defines at least a portion of a cone having an apex.

12. The surgical anchor device recited in claim 11 wherein the apex of the cone is disposed along the axis of the anchor bar.

13. The surgical apparatus adapted to be inserted through a body wall to form an anchor relative to the body wall, comprising:

an introducer having an outer surface;

an anchor bar having a longitudinal configuration and being adapted for disposition in contact with the outer surface of the introducer;

a suture having a first end and a second end, the first end of the suture being attached to the anchor bar with a second end to the suture extending laterally of the anchor bar and outwardly of the outer surface of the introducer; and a pusher movable relative to the outer surface of the introducer to engage the anchor bar and to separate the anchor bar from the outer surface of the introducer.

14. The surgical apparatus recited in claim 13 wherein the anchor bar has a longitudinal side surface and an end surface; and the end surface of the anchor bar defines at least a portion of a cone.

15. The surgical apparatus recited in claim 13 wherein the anchor bar has an inner surface disposed in sliding engagement with the outer surface of the introducer.

16. A surgical anchor device adapted for insertion through a body wall, including:

an anchor bar extending longitudinally along an axis between a proximal end and a distal end, the anchor bar having a side surface extending generally between the proximal end and the distal end of the anchor bar; a suture having a first end and a second end, the first end of the suture having a fixed relationship with the anchor bar and extending from the anchor bar at the side surface of the anchor bar between the distal end and the proximal end; and portions of the anchor bar disposed at the distal end of the anchor bar and defining an outer surface having an inclined relationship with the axis of the anchor bar; whereby the inclined outer surface at the distal end of the anchor bar contacts the body wall and facilitates axial insertion of the anchor device through the body wall.

17. The surgical anchor device recited in claim 16 wherein the portions of the anchor bar define an outer surface configured in the shape of a cone having an apex and a reduced circumference with progressive distal positions along the axis of the anchor bar.

18. The surgical anchor device recited in claim 17 wherein the apex of the cone is disposed at other than the side surface of the anchor bar.

19. The surgical anchor device recited in claim 18 wherein the cone is a right cone and the apex is disposed along the axis of the anchor bar.

20. The surgical anchor device recited in claim 16 wherein the anchor bar is formed from a material which is molded over the first end of the suture to fixedly capture the first end of the suture in the anchor bar.

21. The surgical anchor device recited in claim 20 where in the material of the anchor bar has characteristics for being resorbed.

* * * * *